(12) United States Patent
Fujisawa (10) Patent No.: US 9,603,505 B2
(45) Date of Patent: Mar. 28, 2017

(54) ACTUATOR CONTROL APPARATUS (71) Applicant: OLYMPUS CORPORATION, Tokyo (JP)

(72) Inventor: Yutaka Fujisawa, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/219,460

(22) Filed: Jul. 26, 2016

(65) Prior Publication Data
US 2016/0331211 A1 Nov. 17, 2016

Related U.S. Application Data (63) Continuation of application No. PCT/JP2015/058739, filed on Mar. 23, 2015.

(30) Foreign Application Priority Data

Jun. 20, 2014 (JP) ................. 2014-127533

(51) Int. Cl.
| A61B 5/044 | (2006.01) |
| H02P 1/32 | (2006.01) |
| A61B 1/00 | (2006.01) |
| G01R 31/02 | (2006.01) |
| G02B 23/26 | (2006.01) |
| A61B 1/005 | (2006.01) |
| A61B 1/045 | (2006.01) |
| A61B 1/05 | (2006.01) |
| G02B 7/08 | (2006.01) |
| G02B 23/24 | (2006.01) |

(52) U.S. Cl.
CPC ............ *A61B 1/00027* (2013.01); *A61B 1/00* (2013.01); *A61B 1/005* (2013.01);
(Continued)

(58) Field of Classification Search
CPC ............ A61B 5/061; A61B 5/044; H02P 1/32
See application file for complete search history.

(56) References Cited

U.S. PATENT DOCUMENTS

2008/0278590 A1* 11/2008 Tanimura ................. G03B 3/10
348/208.99
2013/0175322 A1* 7/2013 Yates ............... A61B 17/07207
227/180.1
(Continued)

FOREIGN PATENT DOCUMENTS

JP H05-146058 A 6/1993
JP H09-242589 A 9/1997
(Continued)

OTHER PUBLICATIONS

International Search Report dated Jun. 16, 2015 from related PCT/JP2015/058739.

*Primary Examiner* — Eduardo Colon Santana
*Assistant Examiner* — Charles S Laughlin
(74) *Attorney, Agent, or Firm* — Scully, Scott, Murphy & Presser, PC (57) ABSTRACT

An actuator control apparatus includes: a drive circuit configured to apply a current for causing an actuator to drive a driven body; a constant current circuit and configured to control a current value of the current applied to the actuator by the drive circuit; a sense resistance connectable to the drive circuit and in which the current passing through the actuator flows; a change-over switch configured to switch a connection destination of the drive circuit from the constant current circuit to the sense resistance in a predetermined period in a current application period in which the current is applied to the actuator by the drive circuit; and an FPGA configured to detect a resistance value of predetermined circuits including the actuator through which the current passes, based on the current flowing in the sense resistance, and configured to detect an abnormality of the actuator based on the detection result.

7 Claims, 6 Drawing Sheets

(52) U.S. Cl.
CPC .......... *A61B 1/00188* (2013.01); *A61B 1/045* (2013.01); *A61B 1/05* (2013.01); *G01R 31/02* (2013.01); *G01R 31/025* (2013.01); *G02B 7/08* (2013.01); *G02B 23/243* (2013.01); *G02B 23/26* (2013.01)

(56) References Cited

U.S. PATENT DOCUMENTS

| | | | |
|---|---|---|---|
| 2013/0193188 A1* | 8/2013 | Shelton, IV | A61B 17/068 227/175.2 |
| 2013/0193189 A1* | 8/2013 | Swensgard | A61B 17/068 227/176.1 |
| 2013/0248576 A1* | 9/2013 | Laurent | A61B 17/07207 227/175.1 |
| 2013/0313304 A1* | 11/2013 | Shelton, IV | A61B 17/072 227/176.1 |
| 2014/0094808 A1* | 4/2014 | Herndon | A61B 5/053 606/80 |
| 2014/0107640 A1* | 4/2014 | Yates | A61B 17/07207 606/33 |

FOREIGN PATENT DOCUMENTS

| | | |
|---|---|---|
| JP | 2000-019428 A | 1/2000 |
| JP | 2006-349527 A | 12/2006 |

* cited by examiner

FIG. 6

ACTUATOR CONTROL APPARATUS

CROSS REFERENCE TO RELATED APPLICATION

This application is a continuation application of PCT/JP2015/058739 filed on Mar. 23, 2015 and claims benefit of Japanese Application No. 2014-127533 filed in Japan on Jun. 20, 2014, the entire contents of which are incorporated herein by this reference.

BACKGROUND OF THE INVENTION

1. Field of the Invention

The present invention relates to an actuator control apparatus, and particularly, to an actuator control apparatus capable of sensitively sensing an abnormality of an actuator.

2. Description of the Related Art

Conventionally, an endoscope system including an endoscope configured to pick up an image of an object inside of a subject, a processor configured to generate an observation image of the object picked up by the endoscope, and the like is widely used in a medical field, an industrial field, and the like.

In the endoscope, an actuator configured to move a focus adjustment lens mounted on a distal end to a desired position is provided at a distal end of an insertion portion. On the other hand, the processor is provided with an actuator control apparatus configured to generate a drive signal for driving the actuator and sense an abnormality of the actuator.

For example, Japanese Patent Application Laid-Open Publication No. 9-242589 discloses an electromagnetic actuator drive circuit configured to apply a weak current to an actuator in a non-drive period of the actuator and detect a change in a current value or a voltage value to thereby perform abnormality sensing of the actuator.

SUMMARY OF THE INVENTION

An aspect of the present invention includes an actuator control apparatus including: a drive control circuit configured to apply a current for causing an actuator to drive a driven body, to the actuator configured to drive the driven body by receiving the current; a current control section connectable to the drive control circuit and configured to control a current value of the current applied to the actuator by the drive control circuit; a sense resistance connectable to the drive control circuit and in which the current passing through the actuator flows; a switch section configured to switch a connection destination of the drive control circuit from the current control circuit to the sense resistance in a predetermined period in a current application period in which the current is applied to the actuator by the drive control circuit; a power supply section configured to supply a voltage to the drive control circuit such that current values of the current applied to the actuator are equal when the switch section switches the connection destination of the drive control circuit from the current control section to the sense resistance; and an abnormality detection section configured to detect a resistance value of predetermined circuits including the actuator through which the current passes, based on the current flowing in the sense resistance, and configured to detect an abnormality of the actuator based on the detection result.

DETAILED DESCRIPTION OF THE PREFERRED EMBODIMENTS

Hereinafter, embodiments of the present invention will be described with reference to the drawings.

First Embodiment

Figure 1:
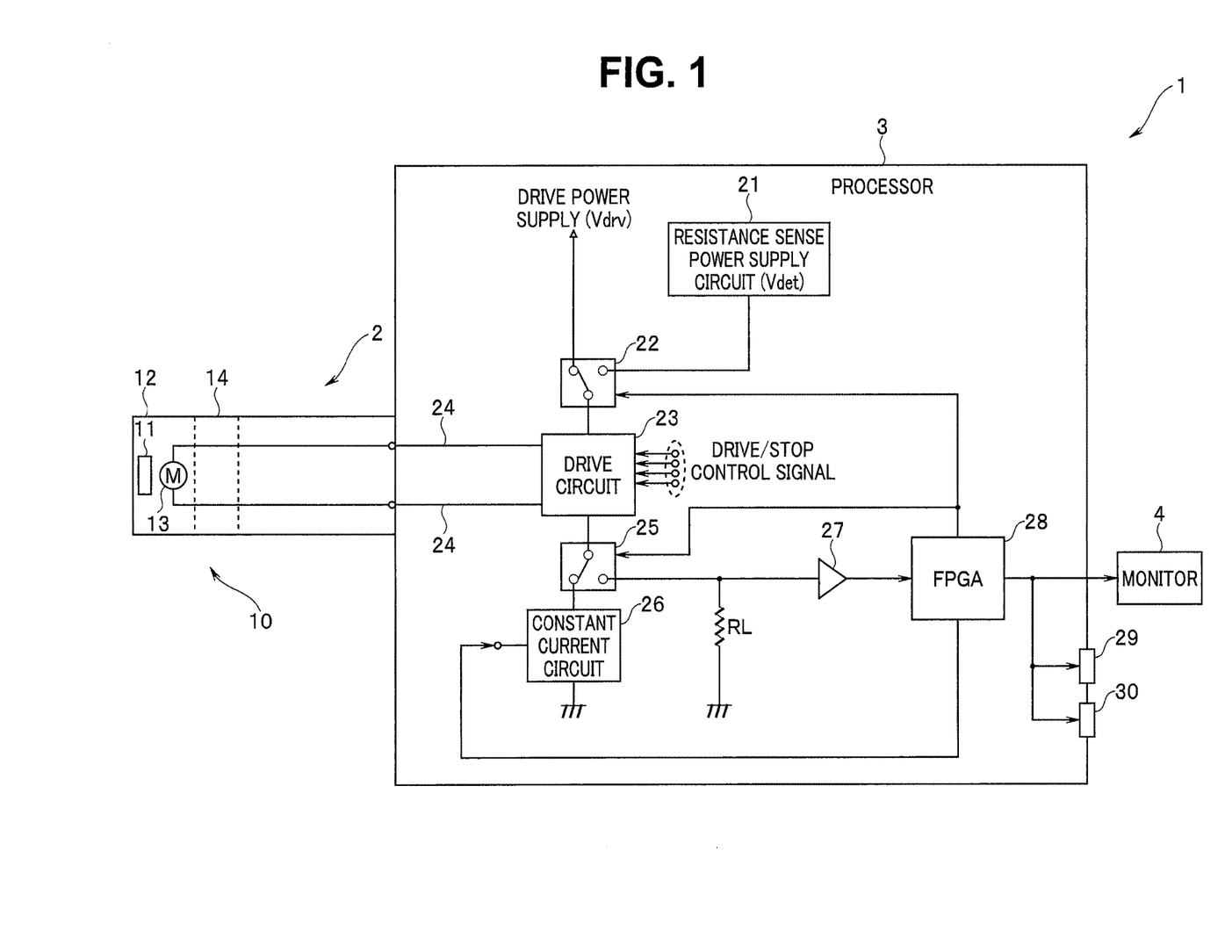
FIG. 1 is a diagram showing a configuration of an endoscope system according to a first embodiment.

First, a configuration of an endoscope system according to a first embodiment will be described with reference to FIG. 1. FIG. 1 is a diagram showing a configuration of an endoscope system according to the first embodiment.

As shown in FIG. 1, an endoscope system 1 includes an endoscope (scope) 2, a processor 3, and a monitor 4. The endoscope 2 includes an elongated insertion portion 10 inserted into a subject and is detachably connected to the processor 3 through a connector not shown provided on a proximal end side of the insertion portion 10.

The insertion portion 10 includes a distal end portion 12 provided with an image pickup device 11 configured to pick up an image of the object. The distal end portion 12 is provided with an actuator 13 including, for example, an electromagnetic coil, the actuator 13 configured to move a focus adjustment lens provided on the distal end portion 12 in a desired direction. A bending portion 14 configured to bend the distal end portion 12 in a desired direction is provided on a proximal end side of the distal end portion 12. Note that although the actuator 13 includes the electromagnetic coil in the description, the actuator 13 is not limited to this. Although the actuator 13 is provided on the distal end portion 12, the arrangement is not limited to this. For example, the actuator 13 may be provided on an operation portion of the endoscope 2 not shown.

The processor 3 forming an actuator control apparatus of the present embodiment includes: a drive power supply Vdrv configured to supply a power supply voltage to apply a drive current to the actuator 13; a resistance sense power supply circuit 21; a change-over switch 22; a drive circuit 23; energizing cables 24; a change-over switch 25; a constant current circuit 26; a sense resistance RL; an amplification circuit 27; an FPGA 28; a speaker 29; and an LED 30. Note that although not shown, the processor 3 also includes: a drive circuit configured to supply a drive signal to the image pickup device 11; a video processing circuit configured to apply predetermined video processing to an image pickup signal picked up by the image pickup device 11 to display an endoscopic image on the monitor 4; and the like.

A resistance sense timing signal is inputted to the change-over switch 22 and the change-over switch 25 from the FPGA 28. The resistance sense timing signal is a timing signal for sensing a resistance value of the actuator 13, and the change-over switch 22 and the change-over switch 25 switch connection destinations based on respective resistance sense timing signals from the FPGA 28.

More specifically, during drive of the actuator 13, the change-over switch 22 as a first switch section is switched to connect the drive power supply Vdrv for driving the actuator 13 and the drive circuit 23 based on the resistance sense timing signal. During the drive of the actuator 13, the change-over switch 25 as a second switch section is switched to connect the drive circuit 23 and the constant current circuit 26 based on the resistance sense timing signal.

On the other hand, during resistance sensing of the actuator 13, the change-over switch 22 is switched to connect the resistance sense power supply circuit 21 for the resistance sensing of the actuator 13 and the drive circuit 23 based on the resistance sense timing signal. During the resistance sensing of the actuator 13, the change-over switch 25 is switched to connect the drive circuit 23 and the sense resistance RL based on the resistance sense timing signal.

The sense resistance RL is set to a resistance value substantially the same as a resistance value of a combination of the actuator 13 and the energizing cables 24 so that sensitivity of the resistance sensing of the actuator 13 becomes maximum.

In the present embodiment, a resistance sense period for sensing the resistance value of the actuator 13 is set in a drive period of the actuator 13. Therefore, a voltage value of a resistance sense power supply Vdet of the resistance sense power supply circuit 21 is set to a value such that a current in the same level as the drive current for driving the actuator 13 flows in the actuator 13. Note that a magnitude correlation of voltage between the drive power supply Vdrv and the resistance sense power supply Vdet is not unconditionally determined because the voltage value of the resistance sense power supply Vdet is changed by the resistance value of the combination of the actuator 13 and the energizing cables 24, and the magnitude correlation of the actuator 13 is determined by a type and the like of the actuator 13.

The drive circuit 23 is connected to the actuator 13 through the energizing cables 24 when the endoscope 2 is connected to the processor 3. The drive circuit 23 is, for example, an H-bridge circuit including four switching elements (for example, MOSFETs or bipolar transistors). The drive circuit 23 as a drive control circuit turns on/off the four switching elements based on a drive/stop control signal from the FPGA 28 to apply a drive current to the actuator 13 such that the actuator 13 drives a driven body.

The constant current circuit 26 as a current control section is connected to the drive circuit 23 through the change-over switch 25 during the drive of the actuator 13 and controls a current value applied to the actuator 13 by the drive circuit 23 based on a control signal from the FPGA 28.

In the resistance sense period of the actuator 13, the resistance sense timing signal from the FPGA 28 switches the change-over switch 22 to connect the resistance sense power supply circuit 21 and the drive circuit 23 and switches the change-over switch 25 to connect the drive circuit 23 and the sense resistance RL. A voltage sensed by the sense resistance RL in the resistance sense period of the actuator 13 is amplified by the amplification circuit 27 and inputted to the FPGA 28.

The FPGA 28 as an abnormality sense section compares a voltage value of the sense resistance RL and a voltage value of the actuator 13 during a normal state to sense that there is an abnormality in the actuator 13 if a difference value between the respective voltage values is greater than a predetermined value. More specifically, the FPGA 28 is formed by: a potential difference detection section configured to detect a potential change in a voltage dividing point between the resistance of the actuator 13 and the sense resistance RL; a comparison section configured to compare the detection result and a predetermined value; and a judgment section configured to judge presence/absence of an abnormality of the actuator 13 based on the comparison result.

When the FPGA 28 senses that there is an abnormality in the actuator 13, the FPGA 28 outputs an abnormality sense signal to the monitor 4 to indicate and display the abnormality on the monitor 4 and notifies a user of the abnormality of the actuator 13. Note that the FPGA 28 may output the abnormality sense signal to the speaker 29 or the LED 30 and use sound or light to notify the user of the abnormality of the actuator 13.

Next, an action of the endoscope system 1 with the configuration will be described.

During the drive of the actuator 13, the change-over switch 22 is controlled to connect the drive power supply Vdrv and the drive circuit 23 based on the resistance sense timing signal from the FPGA 28. The change-over switch 25 is controlled to connect the drive circuit 23 and the constant current circuit 26 based on the resistance sense timing signal from the FPGA 28. As a result, during the drive of the actuator 13, the drive current for driving the actuator 13 flows through a path of the drive power supply Vdrv, the drive circuit 23, the actuator 13, the constant current circuit 26, and GND.

On the other hand, during the resistance sensing of the actuator 13, the change-over switch 22 is controlled to connect the resistance sense power supply circuit 21 and the drive circuit 23 based on the resistance sense timing signal from the FPGA 28. The change-over switch 25 is controlled to connect the drive circuit 23 and the sense resistance RL based on the resistance sense timing signal from the FPGA 28. As a result, during the resistance sensing of the actuator 13, a current for sensing the resistance value of the actuator 13 flows through a path of the resistance sense power supply circuit 21, the drive circuit 23, the actuator 13, the sense resistance RL, and the GND.

The resistance value of the sense resistance RL is a resistance value substantially the same as the resistance value of the combination of the actuator 13 and the energizing cables 24. When there is an abnormality, such as a short circuit between adjacent winding wires of the actuator 13 formed by an electromagnetic coil, the resistance value of the actuator 13 changes, and the voltage value of the sense resistance RL changes.

The FPGA 28 compares the voltage value and a voltage value during normal time to sense an abnormality of the actuator 13. For example, when there is a short circuit between adjacent winding wires of the electromagnetic coil, the resistance value of the actuator 13 drops, and as a result, the voltage value of the sense resistance RL rises. The FPGA 28 senses the abnormality of the actuator 13 from such a change in the voltage value. When the FPGA 28 senses the abnormality of the actuator 13, the FPGA 28 outputs the abnormality sense signal to the monitor 4 and notifies the user of the abnormality of the actuator 13.

Figure 2:
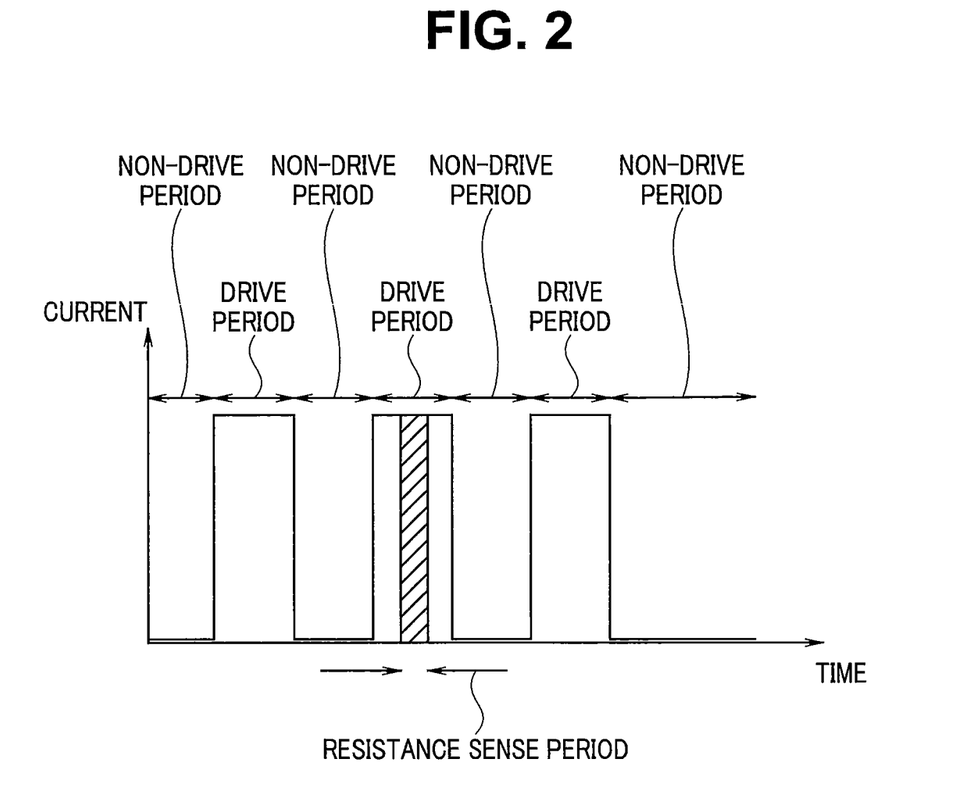
FIG. 2 is a diagram for describing a resistance sense timing of the first embodiment.

FIG. 2 is a diagram for describing a resistance sense timing of the first embodiment.

As shown in FIG. 2, the resistance sense period of the actuator 13 is set to a predetermined period of the drive period of the actuator 13. In the drive period of the actuator 13, the connection destinations of the change-over switch 22 and the change-over switch 25 are switched by the resistance sense timing signal from the FPGA 28 to apply the current through the path of the resistance sense power supply circuit 21, the drive circuit 23, the actuator 13, the sense resistance RL, and the GND.

As described, the voltage value is set in the resistance sense power supply circuit 21 so that the current in the same level as the drive current of the actuator 13 (current flowing in the drive period) flows, and a malfunction does not occur in the actuator 13 in the resistance sense period.

In this way, the processor 3 forming the actuator control apparatus of the present embodiment is configured to switch the connection destinations of the change-over switch 22 and the change-over switch 25 in the drive period of the actuator 13 to provide the resistance sense period. The processor 3 is configured to apply the current in the same level as the drive current of the actuator 13 to the actuator 13 in the resistance sense period.

Conventionally, the resistance sense period of the actuator is provided in a non-drive period in which the actuator is not driven. However, in this case, only a weak current can be applied to the actuator to prevent a malfunction of the actuator. Therefore, a minute change in the resistance value of the actuator, such as a short circuit between adjacent winding wires, cannot be sensed.

On the other hand, in the processor 3 of the present embodiment, the resistance sense period of the actuator 13 is provided in the drive period of the actuator 13, and the current in the same level as the drive current of the actuator 13 is applied to the actuator 13 in the resistance sense period. Therefore, a large current in the same level as the drive current can be applied to the actuator 13 in the resistance sense period. This can improve sensing sensitivity of the resistance value of the actuator 13 and easily sense a minute change in the resistance value of the actuator 13 as an abnormality. As a result, a minute reduction in the resistance value caused by a short circuit between adjacent winding wires of the actuator 13 formed by an electromagnetic coil and the like can be sensitively sensed.

Since the current in the same level as the drive current of the actuator 13 flows in the resistance sense period, the processor 3 can easily control the drive of the actuator 13 without causing a malfunction of the actuator 13. Since the current in the same level as the drive current of the actuator 13 flows in the resistance sense period, the possibility of a malfunction of the actuator 13 is low even if the processor 3 is affected by a disturbance (impulsive force, electromagnetic noise) in the resistance sense period. Note that the processor 3 can also sense a change in the resistance value of the actuator 13 caused by a degradation over time, other than the short circuit between adjacent winding wires of the electromagnetic coil.

Therefore, according to the actuator control apparatus of the present embodiment, a minute change in the resistance value of the actuator can be sensitively sensed without causing a malfunction of the actuator.

(First Modification)

Next, a first modification of the first embodiment will be described.

Figure 3:
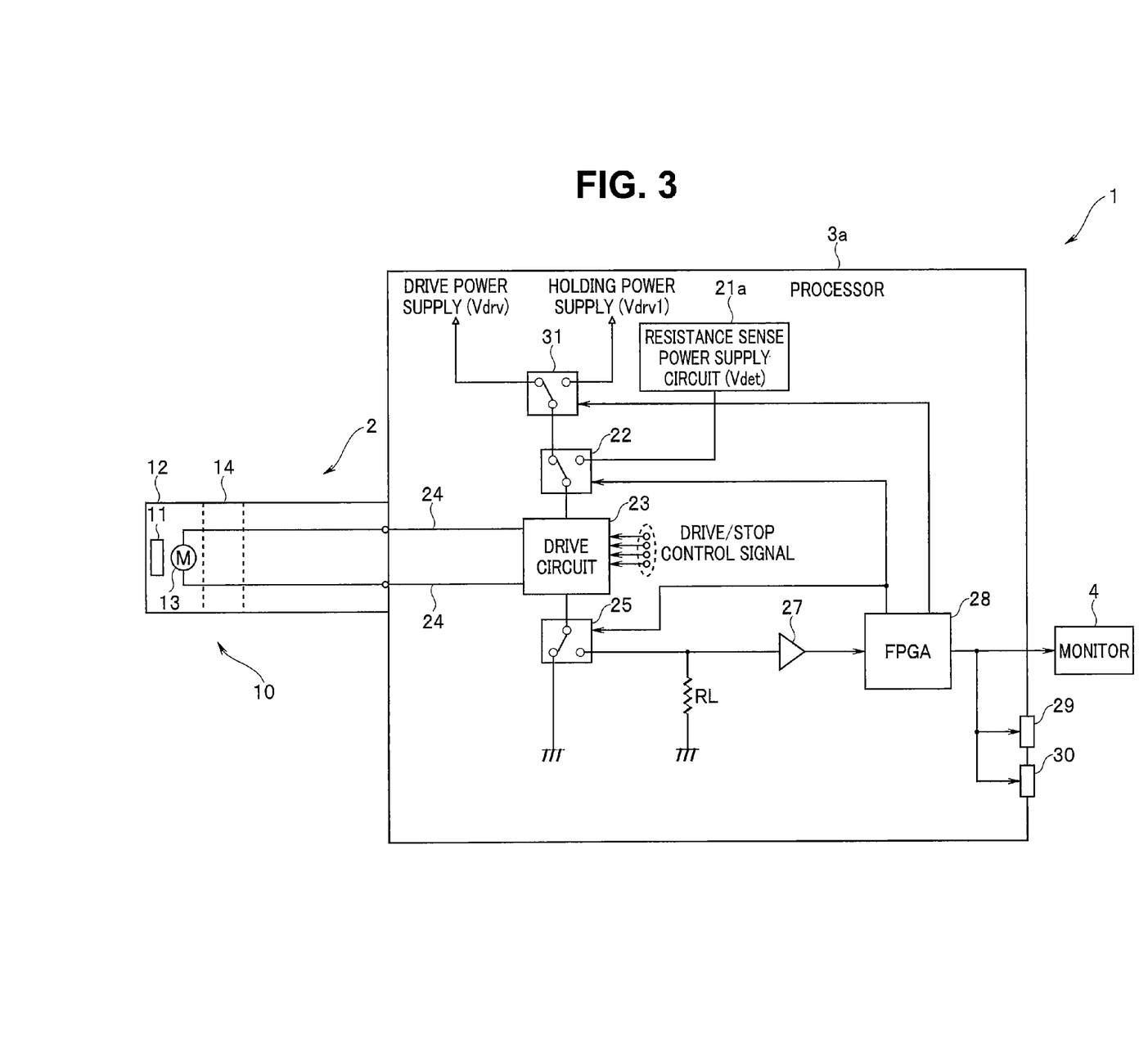
FIG. 3 is a diagram showing a configuration of an endoscope system according to a first modification of the first embodiment.

FIG. 3 is a diagram showing a configuration of an endoscope system according to the first modification of the first embodiment. Note that the same components as in FIG. 1 are designated with the same reference signs in FIG. 3, and the description will not be repeated.

Although the resistance sense period is set in the drive period of the actuator 13 in the embodiment described above, the resistance sense period is set in a holding period of the actuator 13 in the first modification. The holding period of the actuator 13 is a period for holding the actuator 13, that is, a period for holding a position of the focus adjustment lens.

As shown in FIG. 3, the constant current circuit 26 of FIG. 1 is deleted, and a holding power supply Vdrv1 and a change-over switch 31 are added in a processor 3a. Furthermore, the processor 3a uses a resistance sense power supply circuit 21a in place of the resistance sense power supply circuit 21 of FIG. 1.

The holding power supply Vdrv1 is a power supply used for holding the actuator 13, and a voltage value is smaller than the drive power supply Vdrv.

The change-over switch 31 switches a connection destination based on a driving/holding control signal from the FPGA 28. When the driving/holding control signal for driving the actuator 13 is inputted, the change-over switch 31 switches to connect the drive power supply Vdrv and the change-over switch 22. On the other hand, when a driving/holding control signal for holding the actuator 13 is inputted, the change-over switch 31 switches to connect the holding power supply Vdrv1 and the change-over switch 22.

As in the first embodiment, the change-over switch 22 and the change-over switch 25 switch the connection destinations based on the resistance sense timing signal from the FPGA 28. As a result, the drive current flows through a path of the drive power supply Vdrv, the drive circuit 23, the actuator 13, and the GND during the drive of the actuator 13. A holding current flows through a path of the holding power supply Vdrv1, the drive circuit 23, the actuator 13, and the GND during the holding of the actuator 13. The current flows through a path of the resistance sense power supply circuit 21a, the drive circuit 23, the actuator 13, the sense resistance RL, and the GND during the resistance sensing of the actuator 13.

In the present first modification, the resistance sense period for sensing the resistance value of the actuator 13 is set in the holding period of the actuator 13. Therefore, the voltage value of the resistance sense power supply Vdet of the resistance sense power supply circuit 21a is set to a value such that a current in the same level as the holding current for holding the actuator 13 flows in the actuator 13.

A method of the resistance sensing of the actuator 13 is as in the first embodiment. The connection destination of the change-over switch 22 is switched to connect the resistance sense power supply circuit 21a and the drive circuit 23, and the connection destination of the change-over switch 25 is switched to connect the drive circuit 23 and the sense resistance RL in a predetermined period of the holding period of the actuator 13. The FPGA 28 then compares the voltage value of the sense resistance RL with the voltage value at the normal time of the actuator 13 and senses whether there is an abnormality in the actuator 13.

Figure 4:
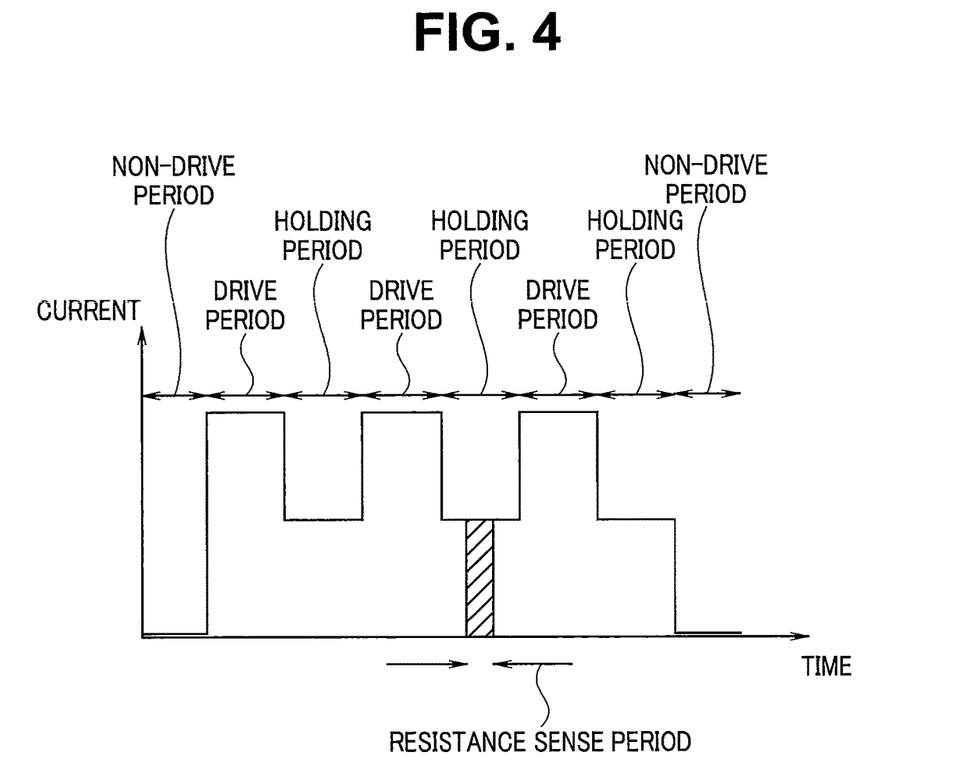
FIG. 4 is a diagram for describing a resistance sense timing of the first modification.

Here, a resistance sense timing of the first modification will be described with reference to FIG. 4. FIG. 4 is a diagram for describing the resistance sense timing of the first modification.

As shown in FIG. 4, the resistance sense period of the actuator 13 is set to a predetermined period in the holding period of the actuator 13. In the holding period of the actuator 13, the connection destinations of the change-over switch 22 and the change-over switch 25 are switched by the resistance sense timing signal from the FPGA 28 to apply the current through a path of the resistance sense power supply circuit 21a, the drive circuit 23, the actuator 13, the sense resistance RL, and the GND.

As described, the voltage value is set in the resistance sense power supply circuit 21a so that the current in the same level as the holding current of the actuator 13 (current flowing in the holding period) flows, and a malfunction does not occur in the actuator 13 in the resistance sense period.

In this way, the processor 3a of the first modification forming the actuator control apparatus is configured to switch the connection destinations of the change-over switch 22 and the change-over switch 25 in the holding period of the actuator 13 to provide the resistance sense period. The processor 3a is configured to apply the current in the same level as the holding current of the actuator 13 to the actuator 13 in the resistance sense period.

Although the holding current applied to the actuator 13 in the holding period is smaller than the drive current of the actuator 13, the holding current is a current greater than the weak current applied in the non-drive period of the actuator 13. Therefore, a large current in the same level as the holding current can be applied to the actuator 13 even when the resistance sense period is set in the holding period of the actuator 13, and the sensing sensitivity of the resistance value of the actuator 13 can be improved as in the first embodiment.

Therefore, according to the actuator control apparatus of the first modification, a minute change in the resistance value of the actuator can be sensitively sensed without causing a malfunction of the actuator as in the first embodiment.

(Second Modification)

Next, a second modification of the first embodiment will be described.

Figure 5:
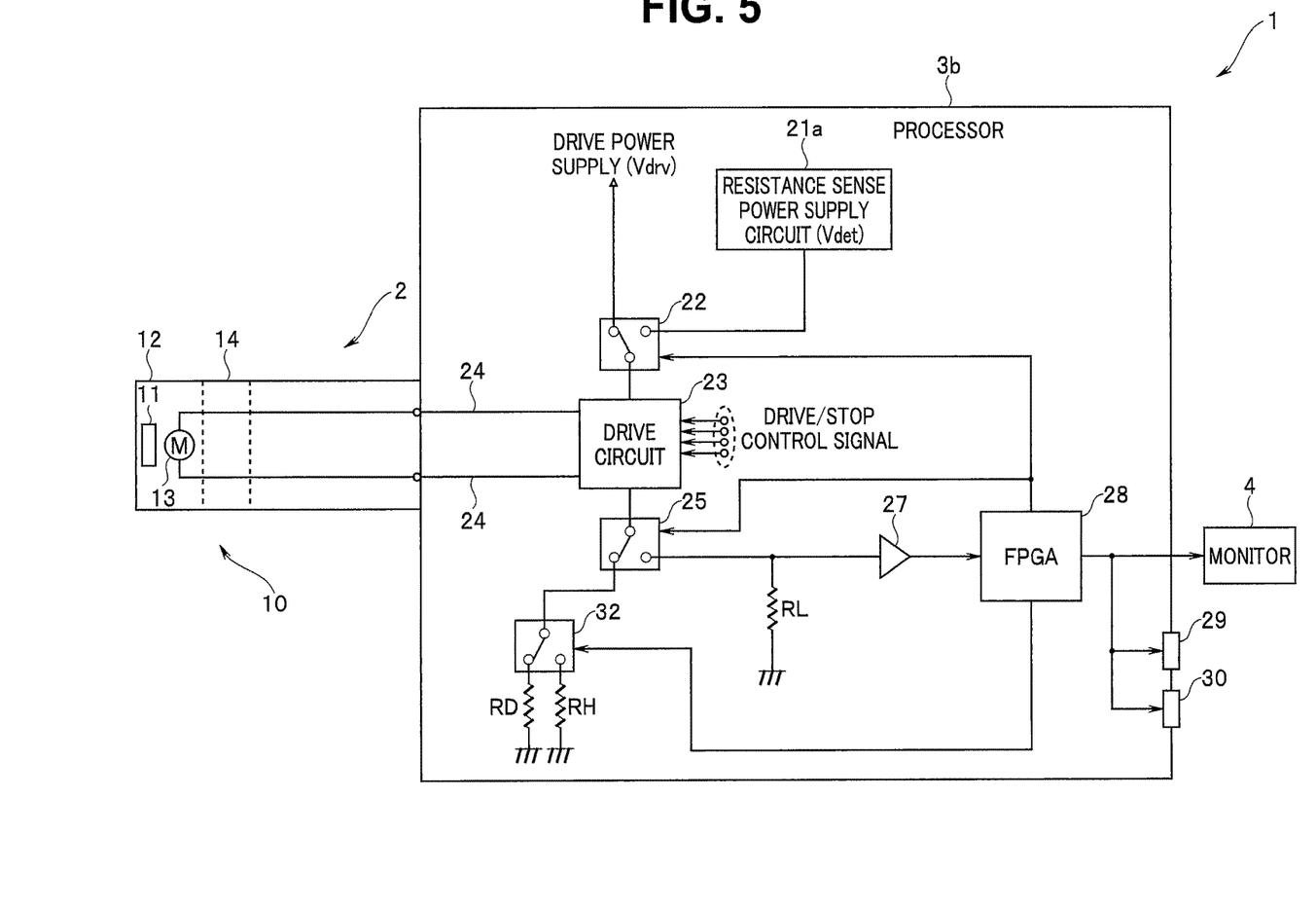
FIG. 5 is a diagram showing a configuration of an endoscope system according to a second modification of the first embodiment.

FIG. 5 is a diagram showing a configuration of an endoscope system according to the second modification of the first embodiment. Note that in FIG. 5, the same components as in FIG. 3 are designated with the same reference signs, and the description will not be repeated.

As shown in FIG. 5, the holding power supply Vdrv1 and the change-over switch 31 of FIG. 3 are deleted, and a change-over switch 32, a drive resistance RD, and a holding resistance RH are added in a processor 3b.

The change-over switch 32 switches a connection destination based on a driving/holding control signal from the FPGA 28. When the driving/holding control signal for driving the actuator 13 is inputted, the change-over switch 32 switches to connect the change-over switch 25 and the drive resistance RD. On the other hand, when the driving/holding control signal for holding the actuator 13 is inputted, the change-over switch 32 switches to connect the change-over switch 25 and the holding resistance RH.

In the present second modification, the drive current and the holding current of the actuator 13 are changed based on a difference between a resistance value of the drive resistance RD and a resistance value of the holding resistance RH. Note that the resistance value of the drive resistance RD may be zero to reduce power consumption of the processor 3b.

The change-over switch 22 and the change-over switch 25 switch the connection destinations based on the resistance sense timing signal from the FPGA 28 as in the first embodiment. As a result, the drive current flows through a path of the drive power supply Vdrv, the drive circuit 23, the actuator 13, the drive resistance RD, and the GND during the drive of the actuator 13. The holding current flows through a path of the drive power supply Vdrv, the drive circuit 23, the actuator 13, the holding resistance RH, and the GND during the holding of the actuator 13.

In the present second modification, the resistance sense period for sensing the resistance value of the actuator 13 is set in the holding period of the actuator 13 as in the first modification (see FIG. 4). Therefore, the voltage value of the resistance sense power supply Vdet of the resistance sense power supply circuit 21a is set to a value such that a current in the same level as the holding current for holding the actuator 13 flows in the actuator 13.

The method of the resistance sensing of the actuator 13 is as in the first modification. The connection destination of the change-over switch 22 is switched to connect the resistance sense power supply circuit 21a and the drive circuit 23, and the connection destination of the change-over switch 25 is switched to connect the drive circuit 23 and the sense resistance RL in a predetermined period of the holding period of the actuator 13. The FPGA 28 then compares the voltage value of the sense resistance RL with the voltage value at the normal time of the actuator 13 and senses whether there is an abnormality in the actuator 13.

As described, the processor 3b of the present second modification can apply a large current in the same level as the holding current to the actuator 13 in the resistance sense period, because the resistance sense period is set in the holding period of the actuator 13 as in the first modification. Therefore, the sensing sensitivity of the resistance value of the actuator 13 can be improved as in the first modification.

Thus, according to the actuator control apparatus of the second modification, a minute change in the resistance value of the actuator can be sensitively sensed without causing a malfunction of the actuator as in the first modification of the first embodiment.

Second Embodiment

Next, a second embodiment will be described.

Figure 6:
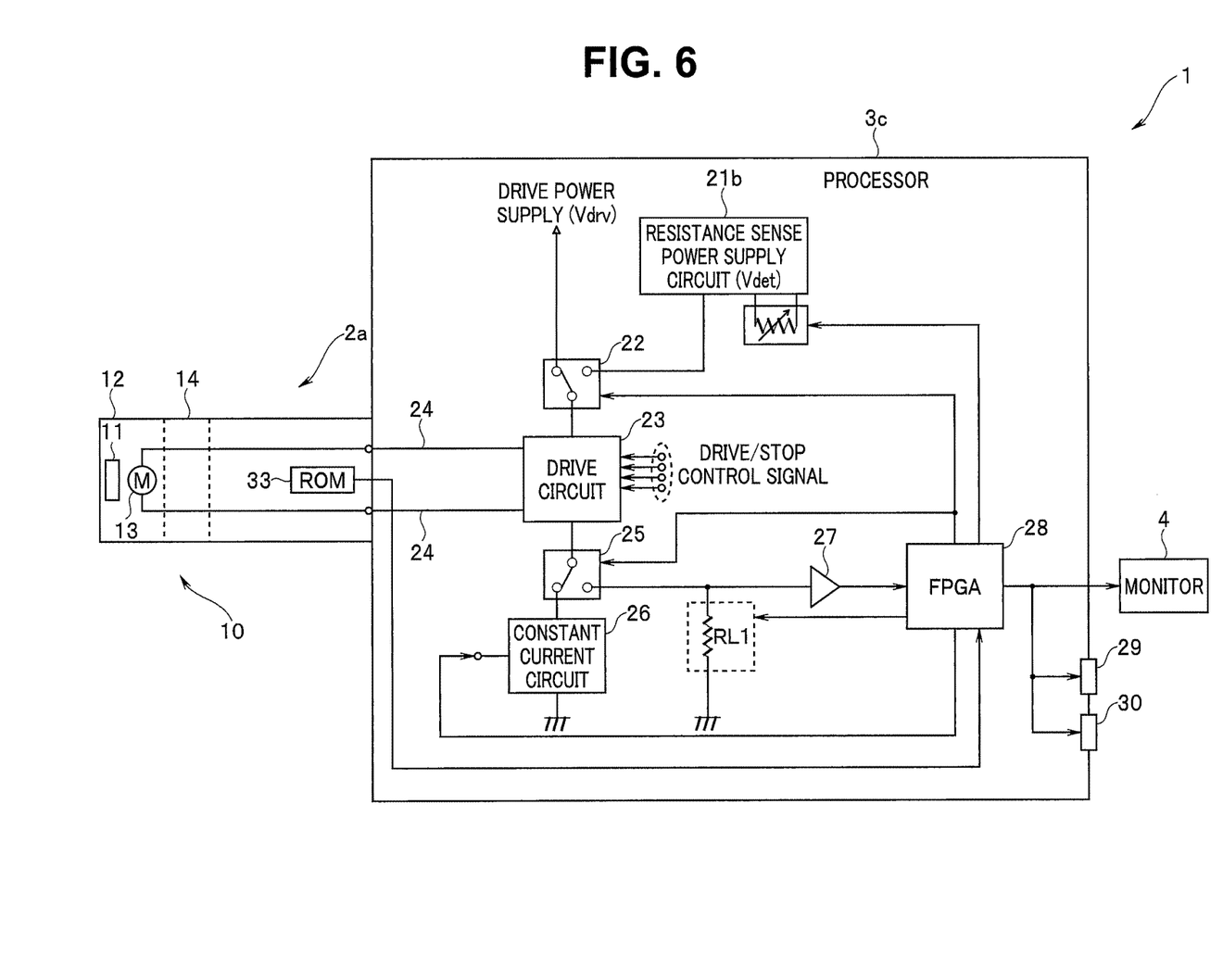
FIG. 6 is a diagram showing a configuration of an endoscope system according to a second embodiment.

FIG. 6 is a diagram showing a configuration of an endoscope system according to the second embodiment. The same components as in FIG. 1 are designated with the same reference signs in FIG. 6, and the description will not be repeated.

As shown in FIG. 6, a ROM 33 storing endoscope information is included in the endoscope 2 of FIG. 1 in an endoscope 2a of the present embodiment. The endoscope information stored in the ROM 33 as a memory section includes at least information of an initial resistance value of the actuator 13, information of presence/absence of the holding period, and information related to the timing of the resistance sense period. Note that the ROM 33 may store information of pulse widths (lengths) of the drive period and the holding period of the actuator 13 and the like.

A processor 3c is formed by using a resistance sense power supply circuit 21b and a potentiometer (sense variable resistance) RL1, each including a variable power supply, in place of the resistance sense power supply circuit 21 and the sense resistance RL of FIG. 1.

The FPGA 28 of the processor 3c reads the endoscope information from the ROM 33 when the endoscope 2a is connected. The FPGA 28 performs variable control of the resistance value of the potentiometer RL1 based on the information of the initial resistance value of the actuator 13 in the endoscope information so that resistance sensing sensitivity becomes maximum. The FPGA 28 also performs variable control of the voltage value of the resistance sense power supply Vdet of the resistance sense power supply circuit 21b based on the information of the initial resistance value of the actuator 13 in the endoscope information so that a current in the same level as the holding current of the actuator 13 flows in the actuator 13 in the resistance sense period.

The FPGA 28 as a control section switches the connection destinations of the change-over switch 22 and the change-over switch 25 and performs the resistance sensing of the actuator 13 at the predetermined period and timing based on the information of the presence/absence of the holding period read from the ROM 33 and the information related to the timing of the resistance sense period.

The method of the resistance sensing of the actuator 13 is as in each of the modifications. The connection destination of the change-over switch 22 is switched to connect the resistance sense power supply circuit 21*b* and the drive circuit 23, and the connection destination of the change-over switch 25 is switched to connect the drive circuit 23 and the potentiometer RL1 in a predetermined period of the holding period of the actuator 13. The FPGA 28 then compares the voltage value of the potentiometer RL1 with the voltage value at the normal time of the actuator 13 and senses whether there is an abnormality in the actuator 13.

Note that when the FPGA 28 judges that there is no holding period based on the information of the presence/absence of the holding period stored in the ROM 33, the FPGA 28 can perform the variable control of the voltage value of the resistance sense power supply Vdet of the resistance sense power supply circuit 21*b* and perform the resistance sensing of the drive period of the actuator 13 as in the first embodiment so that a current in the same level as the drive current of the actuator 13 flows in the actuator 13.

As described, the processor 3*c* is configured to perform the variable control of the resistance value of the potentiometer RL1 and the voltage value of the resistance sense power supply Vdet of the resistance sense power supply circuit 21*b* according to the initial resistance value of the actuator 13 stored in the ROM 33. The processor 3*c* then performs the resistance sensing of the actuator 13 at the predetermined period and timing based on the information of the presence/absence of the holding period stored in the ROM 33 and the information related to the timing of the resistance sense period.

As a result, the processor 3*c* forming the actuator control apparatus of the present embodiment can perform optimal abnormality sensing according to the type of the actuator 13 mounted on the endoscope 2*a*.

Therefore, according to the actuator control apparatus of the present embodiment, a minute change in the resistance value of the actuator can be sensitively sensed without causing a malfunction of the actuator as in the first embodiment.

Since the processor 3*c* performs the variable control of the resistance value of the potentiometer RL1 and the voltage value of the resistance sense power supply Vdet of the resistance sense power supply circuit 21*b* according to the initial resistance value of the actuator 13, the processor 3*c* can sensitively perform the abnormality sensing of the actuator 13 even if there are individual variations in the actuator 13.

Furthermore, since the processor 3*c* performs the variable control of the resistance value of the potentiometer RL1 and the voltage value of the resistance sense power supply Vdet of the resistance sense power supply circuit 21*b* according to the initial resistance value of the actuator 13, the processor 3*c* can sense a degradation of the actuator 13 from initial shipment.

The present invention is not limited to the embodiments and the modifications, and various changes, modifications, and the like can be made without changing the scope of the present invention.

What is claimed is:

1. An actuator control apparatus comprising:
   a drive control circuit configured to apply a current for causing an actuator to drive a driven body, to the actuator configured to drive the driven body by receiving the current;
   a current control section connectable to the drive control circuit and configured to control a current value of the current applied to the actuator by the drive control circuit;
   a sense resistance connectable to the drive control circuit and in which the current passing through the actuator flows;
   a switch section configured to switch a connection destination of the drive control circuit from the current control section to the sense resistance in a predetermined period in a current application period in which the current is applied to the actuator by the drive control circuit;
   a power supply section configured to supply a voltage to the drive control circuit such that current values of the current applied to the actuator are equal when the switch section switches the connection destination of the drive control circuit from the current control section to the sense resistance; and
   an abnormality detection section configured to detect a resistance value of predetermined circuits including the actuator through which the current passes, based on the current flowing in the sense resistance, and configured to detect an abnormality of the actuator based on the detection result.

2. The actuator control apparatus according to claim 1, wherein
   the power supply section comprises at least two constant voltage power supplies, a first constant voltage power supply and a second constant voltage power supply, with different power supply voltages, and
   the actuator control apparatus further comprises a power supply switch section configured to switch the power supply for supplying the voltage to the drive control circuit from the first constant voltage power supply to the second constant voltage power supply when the switch section switches the connection destination of the drive control circuit from the current control section to the sense resistance.

3. The actuator control apparatus according to claim 1, wherein
   the current application period includes a drive period in which the drive control circuit applies a drive current for driving the driven body to the actuator and a holding period in which a holding current for stopping the driven body at a predetermined position is applied, and
   the power supply section supplies the voltage such that the current value of the current applied to the actuator is equal to the drive current in the drive period and equal to the holding current in the holding period when the switch section switches the connection destination of the drive control circuit from the current control section to the sense resistance.

4. The actuator control apparatus according to claim 1, wherein
   the current application period includes only the drive period in which the drive control circuit applies the drive current for driving the driven body to the actuator, and
   the power supply section supplies the voltage such that the current value of the current applied to the actuator is equal to the drive current in the drive period when the switch section switches the connection destination of the drive control circuit from the current control section to the sense resistance.

5. The actuator control apparatus according to claim 1, wherein
a resistance value of the sense resistance is substantially same as the resistance value of the predetermined circuits including the actuator through which the current passes when the switch section switches the drive control circuit to the sense resistance.

6. The actuator control apparatus according to claim 1, wherein
the abnormality detection section further comprises: a potential difference detection section configured to detect a potential change in a voltage dividing point between a resistance of the actuator and the sense resistance; a comparison section configured to compare the detection result and a predetermined value; and a judgment section configured to judge presence/absence of an abnormality of the actuator based on the comparison result.

7. The actuator control apparatus according to claim 3, further comprising
a memory section configured to store information related to a length of the current application period, an initial resistance value of the actuator, presence/absence of the holding period, and a timing of the predetermined period; and
a control section configured to determine a voltage value of the power supply section, the resistance value of the sense resistance, and a length and the timing of the predetermined period based on the information stored in the memory section.

* * * * *